United States Patent [19]

Drent

[11] Patent Number: 4,859,646
[45] Date of Patent: Aug. 22, 1989

[54] PROCESS FOR THE DIMERIZATION OF OLEFINS

[75] Inventor: Eit Drent, Amsterdam, Netherlands

[73] Assignee: Shell Oil Company, Houston, Tex.

[21] Appl. No.: 240,301

[22] Filed: Sep. 6, 1988

Related U.S. Application Data

[62] Division of Ser. No. 156,674, Feb. 17, 1988, Pat. No. 4,806,647.

[30] Foreign Application Priority Data

Feb. 24, 1987 [GB] United Kingdom ............... 8704338

[51] Int. Cl.$^4$ .............................................. B01J 31/02
[52] U.S. Cl. ..................................... 502/165; 502/167
[58] Field of Search ................................ 502/165, 167

[56] References Cited

U.S. PATENT DOCUMENTS

| | | | |
|---|---|---|---|
| 3,711,534 | 1/1973 | Manyik et al. | 260/475 N |
| 3,798,260 | 3/1974 | Hattri et al. | 260/497 A |
| 4,518,814 | 5/1975 | Knudsen et al. | 585/523 |
| 4,528,415 | 7/1985 | Knudsen | 585/527 |
| 4,528,416 | 7/1985 | Lutz | 585/527 |
| 4,634,793 | 1/1986 | Drent | 560/243 |

FOREIGN PATENT DOCUMENTS 0170311  2/1986  European Pat. Off.
1153519  5/1969  United Kingdom.

*Primary Examiner*—Patrick P. Garvin

[57] ABSTRACT

A process for the dimerization of alpha-alkenes having 2 to 12 carbon atoms in the presence of an alkanediol solvent and of a novel catalytic system formed by combining:
(a) a palladium(II) compound,
(b) a chelate ligand comprising a compound containing at least two N coordinating atoms which are connected through a chain comprising two C atoms, >2.0 mol chelate ligand per gram-atom Pd being used,
(c) a protonic acid, except hydrohalogenic acids, and
(d) a salt of Cu, Fe, Zn, Sn, Mn, V, Al or a group VIB metal, except a halide.

1 Claim, No Drawings

PROCESS FOR THE DIMERIZATION OF OLEFINS

This a division of application Ser. No. 156,674, filed Feb. 17, 1988 and now U.S. Pat. No. 4,806,647.

FIELD OF THE INVENTION

The invention relates to a process for the dimerization in the liquid phase of an alpha-alkene having in the range of from 2 to 12 carbon atoms per molecule. The invention also relates to a novel catalytic system.

BACKGROUND OF THE INVENTION

It is known from European Patent Application No. 170,311 to dimerize an alpha-alkene having in the range of from 2 to 12 carbon atoms per molecule in the presence of a catalytic system formed by combining, in the presence of water, an alcohol, or a carboxylic acid:

(a) a palladium(II) compound,
(b) a chelate ligand comprising a compound containing as coordinating atoms at least two nitrogen atoms which are connected through a chain comprising two carbon atoms, and
(c) a compound containing an anion of an acid, with the exception of hydrohalogenic acids.

The reaction mixture obtained by means of this known process may comprise a two-phase liquid system: a liquid dimer phase and a liquid solvent phase containing the catalytic system. Both phases can easily be separated by means of mechanical separation and the separated solvent phase containing the catalytic system can be used for dimerizing further quantities of alpha-alkenes.

It has been observed that the dimer phase contains a portion of the chelate ligand and the solvent phase has a correspondingly reduced content thereof. This reduced content of chelate ligand may lower the catalytic activity of the catalytic system, particularly when considerably less than 2 mol of chelate ligand per gram-atom of palladium(II) remains.

Starting this known process by using more than 2 mol of the chelate ligand per gram-atom of palladium(II) would compensate for said loss of chelate ligand, but renders the catalyst less active.

A novel catalytic system has now been found that is surprisingly active when more than 2 mol of the chelate ligand per gram-atom of palladium are used.

SUMMARY OF THE INVENTION

This invention provides a process for the dimerization in the liquid phase of an alpha-alkene having in the range of from 2 to 12 carbon atoms per molecule in which the dimerization is carried out in the presence of an alkanediol solvent and of a catalytic system formed by combining:

(a) a palladium(II) compound,
(b) a chelate ligand comprising a compound containing as coordinating atoms at least two nitrogen atoms which are connected through a chain comprising two carbon atoms, more than 2.0 mol of the chelate ligand per gram-atom of palladium(II) being used,
(c) a protonic acid, with the exception of a hydrohalogenic acid, and
(d) a salt of copper, iron, zinc, tin, manganese, vanadium, aluminium or of a metal of Group VIB of the Periodic Table of the Elements, with the exception of a halide.

DESCRIPTION OF THE PREFERRED EMBODIMENTS

It has been found that the presence of both the protonic acid and said salts has a synergistic effect on the activity of the catalytic system vis-à-vis the presence of the protonic acid alone and of said salts alone. Simultaneously, a very high selectivity to dimers, usually higher than 95%, has been observed. The selectivity to dimers is defined as the molar percentage of dimers in the product formed.

Alpha-alkenes having in the range of from 2 to 12 carbon atoms which can be used in the process according to the present invention may be linear or branched, such as, for example, ethene, propene, 1-butene, 1-pentene, 1-hexene, 5-methyl-1-hexene, 1-octene and 1-dodecene. The preferred alpha-alkenes are ethene, propene and 1-butene.

The word "dimerization" as it is used herein, refers to the reaction of two identical olefins as well as the reaction of two different olefins. An example of the latter reaction is that between ethene and propene, or between propene and 1-butene.

According to the invention, both homogeneous and heterogeneous catalytic systems can be used. The use of homogeneous catalytic systems is preferred. Palladium(II) compounds which can be used in the process according to the invention therefore preferably comprise palladium(II) compounds which are soluble in the reaction medium or form in-situ soluble compounds therein. Examples of suitable palladium(II) compounds are palladium nitrate, palladium sulfate and palladium carboxylates, preferably carboxylates of carboxylic acids having not more than 12 carbon atoms per molecule. Palladium alkanoates, in particular palladium acetate, are preferably used.

Further examples of suitable palladium compounds are palladium complexes such as bis(2,4-pentanedionato)palladium, bis(picolinato)palladium, tetrakis(triphenylphosphine)palladium, tetrakisacetonitrile palladium tetrafluoroborate, bis(tri-o-tolylphosphine)palladium acetate, bis(triphenylphosphine)palladium sulfate, palladium olefin complexes and palladium-hydride complexes. A mixture of palladium(II) compounds may be present in the catalytic system.

The quantity of the palladium compound used may vary within wide ranges and is generally in the range between $10^{-6}$ and $10^{-1}$ gram-atom palladium per mol olefin starting material. A range between $10^{-5}$ and $10^{-2}$ gram-atom palladium compound is preferred.

Preference is given to chelate ligands containing in the molecule a group of the formula

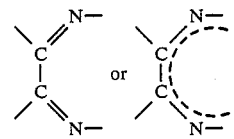

wherein the dotted line represents several kekule resonance structures in case of condensed aromatic ring systems as e.g. occurring in 1,10-phenanthroline. For example, N,N'-1,2-ethanediylidenebisphenylamine, N,N'-1,2-ethanediylidenebis[4-chlorophenylamine], N,N'-1,2-ethanediylidenebis[4-methoxyphenylamine], N-substituted derivatives of 2-pyridinemethanimine, 2,2'-bipyridyl, 4,4'-dimethyl-2,2'-bipyridyl, 4,4'-dichloro-2,2'-bipyridyl, 4,4'-dimethoxy-2,2'-bipyridyl, 1,10-phenanthroline, 5-chloro-1,10-phenanthroline, 4,7-diphenyl-1,10-phenanthroline, 4,7-dimethyl-1,10-phenanthroline, 2,9-dichloro-1,10-phenanthroline, 1,10-phenanthroline-5-sulfonic acid and salts thereof, 4,7-diphenyl-1,10-phenanthrolinedisulfonic acid and salts thereof, and 3,5-cyclohexadiene-1,2-diimine may be used.

The compounds preferably used in the catalytic system used in the process according to the invention are 1,10-phenanthroline or a derivative thereof and 2,2'-bipyridyl or a derivative thereof. Most preferred is 1,10-phenanthroline.

A mixture of chelate ligands such as, for example, a mixture of 1,10-phenanthroline and 2,2'-bipyridyl can be used.

The quantity of chelate ligand used in the catalytic system is at least 2.0 mol per gram-atom of palladium(II) and is preferably in the range of from 2.5 to 25 mol per gram-atom palladium(II).

Any protonic acid, with the exception of hydrohalogenic acids, and any salt of a protonic acid and derived from copper, iron, zinc, tin, manganese, vanadium, aluminum or of a Group IVB metal, with the exception of a halide, may be present. The acid and salt preferably have a non-coordinating anion, by which is meant that little or no covalent interaction takes place between the palladium(II) and the anion. Typical examples of such anions are $PF_6^-$, $SbF_6^-$, $BF_4^-$ and $ClO_4^-$.

The protonic acid and the acid from which the salt is derived preferably have a pKa of less than 3 and, more preferably, less than 2, measured in aqueous solution at a temperature of 18° C.

Preferred protonic acids are sulfonic acids and acids that can be formed, possibly in-situ, by interacting a Lewis acid such as, for example, $BF_3$, $AsF_5$, $SbF_5$, $PF_5$, $TaF_5$ or $NbF_5$ with a Broensted acid such as, for example, a hydrohalogenic acid, in particular HF, fluorosulfonic acid, phosphoric acid or sulfuric acid. Specific examples of acids of the latter type are fluorosilicic acid, $HBF_4$, $HPF_6$ and $HSbF_6$. Examples of suitable sulfonic acids are fluorosulfonic acid and chlorosulfonic acid and the hereinafter specified sulfonic acids.

A preferred group of protonic acids has the general formula I:

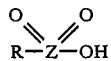 (I)

wherein Z represents sulfur or chlorine and, if Z is chlorine, R represents oxygen and, if Z is sulfur, R represents an OH group or an hydrocarbon group. As used herein, the term "hydrocarbon group" refers to hydrocarbon groups which can be either unsubstituted or substituted, with the substituent being any substituent which does not interfere with the reaction.

When the hereinbefore-stated protonic acids are used in the process according to the invention, the anions of the compounds can be considered to be non-coordinating.

The substituted or unsubstituted hydrocarbon group represented by R is preferably an alkyl, aryl, aralkyl or alkaryl group having 1 to 30, in particular 1 to 14, carbon atoms. The hydrocarbon group may, for example, be substituted with the halogen atoms, in particular, fluorine atoms. Examples of suitable acids of the general formula I are perchloric acid, sulfuric acid, 2-hydroxypropane-2-sulfonic acid, benzenesulfonic acid, 1- and 2-naphthalenesulfonic acid, p-toluenesulfonic acid and trifluoromethanesulfonic acid, the last two acids being the most preferred.

Examples of suitable carboxylic acids are formic acid, acetic acid, monochloroacetic acid, dichloroacetic acid, trichloroacetic acid and, preferably, trifluoroacetic acid.

A mixture of protonic acids may be present in the catalytic system.

Among the salts that are present preference is given to copper and iron salts, such salts imparting a very high activity to the catalytic system. Among the Group VIB metals, chromium is preferred.

A mixture of two or more of the metals may be present such as, for example, copper and iron, or, copper and vanadium.

Among the salts, sulfates, p-tosylates and tetrafluoroborates are preferred. Very good results have been obtained with sulfates and p-tosylates. The protonic acid and the salt may have the same or different anions. For example, a mixture of p-toluenesulfonic acid and a sulphate may be used.

The protonic acid and the salt are preferably used in a total quantity in the range of from 0.01 to 150 and in particular 1 to 100 equivalents per gram-atom palladium.

The amount of protonic acid which is used per equivalent of salt is not critical and may vary within wide ranges. Preferably, in the range of from 0.1 to 10 equivalents of the protonic acid per equivalent of said salt is used. However, amounts of less than 0.1 and more than 10 equivalents are not excluded.

It will be appreciated that when the catalytic system applied in the process according to the invention is formed by combining in-situ the required ingredients, a palladium complex compound with catalytic activity may be formed in the reaction mixture. An example of such a compound is palladium bis(1,10-phenanthroline)-diperchlorate or ditosylate. The use of such a palladium complex compound when prepared separately as a catalytic system is within the scope of the present invention.

In the process of the invention, the catalytic system is used in the presence of an alkanediol solvent. Very good results have been obtained with ethylene glycol. Other examples of suitable alkanediol solvents are 1,2-propanediol, 1,3-propanediol, 1,4-butanediol, 1,2-butanediol, 1,6-hexanediol and polyethylene glycols such as diethylene glycol. The presence of a co-solvent is not excluded. Examples of co-solvents are alcohols, carboxylic acids and water. The alcohols or carboxylic acids may be aliphatic, cycloaliphatic or aromatic and may be substituted with one or more substituents, for example alkoxy, cyano or ester groups or halogen atoms. The alcohols or carboxylic acids preferably contain not more than 20 carbon atoms per molecule. Examples of suitable alcohols are methanol, ethanol, propanol, isobutyl alcohol, tertiary butyl alcohol, stearyl alcohol, benzyl alcohol, cyclohexanol, allyl alcohol and chlorocapryl alcohol.

Further examples of co-solvents are hydrocarbons such as, for example, hexane and in particular aromatic hydrocarbons such as benzene or toluene; halogenated hydrocarbons such as chloroform, chlorobenzene or perfluoroalkanes; ketones such as actone, diethyl ketone or methyl isobutyl ketone; ethers such as tetrahydrofuran, dimethyl ether of diethylene glycol (also referred to as "diglyme"), methyl t-butyl ether or 1,4-dioxane; sulfones such as dimethyl sulfone, methyl butyl sulfone, tetrahydrothiophene 1,1-dioxide (also referred to as "sulfoane"), and sulfoxides such as dimethyl sulfoxide or diethyl sulfoxide.

The process according to the present invention can be carried out at temperatures of up to 200° C. and preferably in the range between 20° C. and 135° C. The pressure preferably lies between 1 and 100, in particular between 20 and 75, bar gauge.

The process according to the invention can be carried out batchwise, semi-continuously or continuously. The reaction time may vary in relation to the temperature used, between 0.5 and 20 hours.

The dimers may be isolated from the reaction mixture obtained in any suitable manner, for example by mechanically separating the reaction mixture into a liquid dimer phase and a liquid solvent phase. The liquid dimer phase may then be separated by distillation. The dimers are suitable as a feedstock for hydroformylation processes wherein an alkene or a mixture of alkenes is reacted with hydrogen and carbon monoxide in the presence of a hydroformylation catalyst, to produce aldehydes and/or alcohols. Where the product is mainly aldehyde a separate hydrogenation is required to form alcohols. The products obtained by the process according to the present invention require only distillation to separate unconverted mono-olefin and heavy ends before use in a hydroformylation process.

The invention further provides a novel catalytic system formed by combining:
(a) a palladium(II) compound,
(b) a chelate ligand comprising a compound containing as coordinating atoms at least two nitrogen atoms which are connected through a chain comprising two carbon atoms, more than 2.0 mol of the chelate ligand per gram-atom of palladium(II) being used,
(c) a protonic acid, with the exception of a hydrohalogenic acid, and
(d) a salt of copper, iron, zinc, tin, manganese, vanadium, aluminium or of a metal of Group VIB of the Periodic Table of the Elements, with the exception of a halide.

The following Examples are intended to further illustrate the invention and are not to be construed as limiting the scope of the invention. In all Examples, the hexenes formed had a linearity of about 60%.

EXAMPLES 1-9

A 300 ml magnetically stirred Hastelloy C autoclave ("Hastelloy" is a trade mark) was charged with ethylene glycol (50 ml), palladium(II) acetate (0.5 mmol), 1,10-phenanthroline (2 mmol) and p-toluenesulfonic acid (2 mmol). In each of these nine examples, the autoclave was also charged with a salt, as detailed in Table 1 hereinafter. This table also shows the amounts in which these salts were used. The autoclave was then flushed with propene, charged with 50 ml of liquid propene and heated to a temperature of 80° C. After the reaction time indicated in Table 1, the contents of the autoclave were analyzed by gas/liquid chromatography.

Table 1 presents the conversion of propene and the selectivity to hexenes. The selectivity to nonenes is the difference between 100% and the selectivity to hexenes.

TABLE 1

| Example | Salt | mmol of salt | Reaction time, h | Conversion, % | Selectivity, %, to hexenes |
|---|---|---|---|---|---|
| 1 | Cu(p-tosylate)$_2$ | 0.5 | 5 | 70 | 88.2 |
| 2 | " | 1.0 | 1 | 85 | 96.6 |
| 3 | FeSO$_4$ | 1.0 | 1 | 85 | 95.3 |
| 4 | Cr$_2$(SO$_4$)$_3$ | 0.67 | 2 | 75 | 96.4 |
| 5 | ZnSO$_4$ | 0.5 | 2 | 75 | 96 |
| 6 | SnSO$_4$ | 1.0 | 2 | 75 | 96.4 |
| 7 | MnSO$_4$ | 1.0 | 2 | 65 | 97.3 |
| 8 | VOSO$_4$ | 1.0 | 1 | 60 | 97 |
| 9 | Al$_2$(SO$_4$)$_3$ | 0.67 | 2 | 40 | 98.7 |

EXAMPLE 10

Example 2 was repeated with the difference that the temperature was 75° C. instead of 80° C. The conversion of propene was 80% after 5 hours and the selectivities to hexenes and nonenes were 86.7% and 13.3%, respectively.

Comparative Experiment A

Example 2 1 was repeated with the difference that copper(p-tosylate)$_2$ was not present and that 4 mmol instead of 2 mmol of p-toluenesulfonic acid was used.

After 5 hours a conversion of propene of only 10% was observed.

Comparative Experiment B

Example 2 was repeated with the difference that p-toluenesulfonic acid was not present and that 2.0 mmol instead of 1.0 mmol of copper(p-tosylate)$_2$ was used.

After 5 hours a conversion of propene of only 35% was observed. Prolonging the reaction time beyond 5 hours did not further increase the conversion.

Comparative Experiment C

Example 2 was repeated with the difference that Zr(SO$_4$)$_2$ (1 mmol) instead of Cu(p-tosylate)$_2$ (1.0 mmol) was used.

After 5 hours a propene conversion of only 10% was observed.

Comparative Experiment D

Example 2 was repeated with the difference that UO$_2$SO$_4$ (1 mmol) instead of Cu(p-tosylate)$_2$ (1.0 mmol) was used.

The conversion of propene was less than 5% after 5 hours.

Comparative Experiment E

Example 3 was repeated with the difference that p-toluenesulfonic acid (2 mmol) was not present and that 2 mmol FeSO$_4$ instead of 1 mmol FeSO$_4$ was present.

The conversion of propene was less than 5% after 5 hours.

Comparative Experiment F

Example 3 was repeated with the difference that NiSO$_4$ (1.0 mmol) instead of FeSO$_4$ (1.0 mmol) was present.

The conversion of propene was less than 10% after 5 hours.

I claim:

1. A catalytic system which comprises:
   (a) a palladium(II) compound,
   (b) a chelate ligand comprising a compound containing as coordinating atoms at least two nitrogen atoms which are connected through a chain comprising two carbon atoms, wherein more than about 2.0 mol of said chelate ligand per gram-atom of palladium(II) is used,
   (c) a protonic acid, with the exception of a hydrohalogenic acid, and
   (d) a salt of a protonic acid selected from the group consisting of copper, iron, zinc, tin, manganese, vanadium, aluminum, a metal of Group VIB of the Periodic Table of the Elements and mixtures thereof, with the exception of a halide.

* * * * *